(12) United States Patent
Kraemer et al.

(10) Patent No.: US 9,125,712 B2
(45) Date of Patent: Sep. 8, 2015

(54) METHOD IN THE MAKING OF A DENTAL RESTORATION

(75) Inventors: Michael A. Kraemer, Landsberg am Lech (DE); Till Meurer, Worthsee (DE)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 367 days.

(21) Appl. No.: 13/699,041

(22) PCT Filed: May 18, 2011

(86) PCT No.: PCT/US2011/036928
§ 371 (c)(1),
(2), (4) Date: Nov. 20, 2012

(87) PCT Pub. No.: WO2011/149731
PCT Pub. Date: Dec. 1, 2011

(65) Prior Publication Data
US 2013/0073265 A1    Mar. 21, 2013

(30) Foreign Application Priority Data

May 27, 2010    (EP) .................................... 10163996

(51) Int. Cl.
*G06G 7/48*    (2006.01)
*A61C 13/00*    (2006.01)
*A61C 19/05*    (2006.01)

(52) U.S. Cl.
CPC ............ *A61C 13/0004* (2013.01); *A61C 19/05* (2013.01)

(58) Field of Classification Search
CPC .. A61C 7/0002; A61C 13/0004; A61C 19/05; G06F 19/12

USPC ............................................................ 703/6
See application file for complete search history.

(56) References Cited

U.S. PATENT DOCUMENTS

| 6,431,871 | B1 | 8/2002 | Luthardt |
| 2002/0119423 | A1* | 8/2002 | Chishti et al. ................. 433/213 |
| 2005/0095552 | A1 | 5/2005 | Sporbert |
| 2005/0196724 | A1 | 9/2005 | Miller |
| 2006/0127848 | A1* | 6/2006 | Sogo et al. .................... 433/173 |
| 2006/0263739 | A1 | 11/2006 | Sporbert |
| 2009/0068617 | A1 | 3/2009 | Lauren |
| 2010/0316972 | A1 | 12/2010 | Klare |

FOREIGN PATENT DOCUMENTS

DE    19642247    1/1998
DE    102007014088    9/2008
(Continued)

OTHER PUBLICATIONS

Kunii et al., (1994), *Displays*, 15(3):181-188. "Articulation simulation for an Intelligent Dental Care System."
(Continued)

*Primary Examiner* — Dwin M Craig

(57) ABSTRACT

One embodiment of the present disclosure is directed to a method used in the making of a dental restoration, which comprises the steps of determining a tooth flat at a patient's tooth, and evaluating the tooth flat to provide a geometric characteristic data of the first tooth flat. The characteristic data are used to provide a computer model of a jaw motion under occlusal contact between teeth in the patient's upper and lower jaws. In one embodiment, the method helps facilitating the preparation of dental restorations.

13 Claims, 2 Drawing Sheets

(56) References Cited

FOREIGN PATENT DOCUMENTS

| WO | WO 00/10482 | 3/2000 |
| WO | WO 2008/103024 | 8/2008 |

OTHER PUBLICATIONS

Mehl et al., (1997), *Deutsche Zahnaerztliche*, 52(8):520-524. "Erzeugung von CAD-Datensätzen für Inlays and Kronen mit funktionellen Kauflächen." with English Summary.

\* cited by examiner

METHOD IN THE MAKING OF A DENTAL RESTORATION

CROSS REFERENCE TO RELATED APPLICATIONS

This application is a national stage filing under 35 U.S.C. 371 of International Application No. PCT/US2011/036928, filed May 18, 2011, which claims priority to European Application No. 10163996.1, filed May 27, 2010. The disclosures of both applications are incorporated by reference in their entirety herein.

FIELD OF THE INVENTION

The invention relates to a method in the making of a dental restoration, and in particular to a method of determining a jaw motion which is possible under occlusal contact between teeth in the patient's upper and lower jaws.

BACKGROUND ART

The shape of a dental restoration is typically determined dependent on the shape of at least one tooth that neighbors a tooth or teeth to be restored. Such a neighboring tooth may be an adjacent tooth of the tooth to be restored in the same jaw or an opposite tooth of the tooth to be restored in the opposing jaw. Further at least part of the shape of the tooth to be restored may eventually be used to determine the shape of the restoration if residual structure of that tooth is present.

Further for determining the shape of the dental restoration the possible movements of the upper and lower jaws must typically be accounted for, particularly when the jaws are closed so that at least one tooth of the upper jaw is in contact with a tooth of the lower jaw. Such a situation is typically referred to as the teeth being in "occlusal contact" in dentistry. This is because opposing teeth in a patient's mouth typically frequently contact each other in different positions relative to one another, for example during chewing. Therefore a good fit between the restoration and an opposing tooth or opposing teeth must be ensured not only in one position but rather in various positions of the jaws relative to one another. Further the jaws can typically be moved relative to one another with the teeth remaining in occlusal contact, as it also often occurs for example during chewing. Such a movement of the jaws relative to one another with the teeth being in occlusal contact is typically referred to as "articulation" in dentistry. Therefore for the preparation of a dental restoration the articulation is typically determined and simulated for precisely fitting the dental restoration to one or more opposing teeth.

There are various methods for simulating the articulation, one of which comprises manual articulation by use of a mechanical articulator. Such a mechanical articulator typically reproduces the human upper and lower jaws which are movably connected by a joint. The reproduced jaws are further adapted to receive models of a patient's jaw that also represent the patient's teeth so that the articulation can be simulated. The dental restoration may be placed in a model to test its fit relative to neighboring teeth under simulated articulation. The joint of such an articulator is typically designed to resemble the mechanical interaction of the bones forming the joint. That joint is typically referred to as "temporomandibular joint" in dentistry. The mechanical interaction of bone joints is more complex that a simple mechanical hinge, and in particular may provide for a movement which deviates from an ideally circular movement around a pivot axis as provided by a hinge. Further a bone joint may also allow movements radially and axially from the pivot axis. There are different articulators which resemble the temporomandibular joint at different quality. Articulators that are designed to more precisely resembling the temporomandibular joint are often also more complex in use and more expensive than other articulators having a simpler configuration.

Because the precision of a simulated articulation may be important to provide a precisely fitting dental restoration approaches have been developed which include the use of computers.

For example U.S. Pat. No. 6,431,871 B1 discloses a method which comprises the steps of producing casts of the upper and lower jaw from an impression, coordinating them using an articulator, coordinating reference points on the jaw casts with the rotation axis of the articulator, arranging the jaw casts in a measuring device for determining the geometry of the tooth to be restored and the rotation axis of the articulator by use of the reference points, digitizing the jaw casts, and constructing the denture using CAD, and manufacturing the denture using CAM.

US 2009/0068617 A1 discloses methods for acquiring and utilizing time-based 3D jaw motion images to enhance the computer-aided design of dental restorations. The 3D jaw motion images are used to provide a jaw motion model for driving a motion simulation which is used in a computer-aided design of a dental restoration.

Although existing approaches may provide certain advantages there is still a need for facilitating the preparation of dental restorations which precisely fit and cooperate with other teeth in a patient's mouth. Desirably such dental restorations can be prepared largely outside of a patient's mouth and require minimized or no mechanical finishing in shape after placement in the patient's mouth. Further it is desirable that such dental restorations are relatively inexpensive.

SUMMARY OF THE INVENTION

In one aspect the invention relates to a method in the making of a dental restoration, and in particular to a method of determining an articulation. The method comprises the steps of:
  determining a first tooth flat at a representation of a first patient's tooth;
  evaluating the first tooth flat to provide characteristic data representing at least one geometric characteristic of the first tooth flat;
  using the characteristic data to calculate a computer model of the patient's possible jaw motion under occlusal contact between teeth in the patient's upper and lower jaws.

An alternative method comprises the steps of:
  determining a first tooth flat at a first patient's tooth;
  evaluating the first tooth flat to provide characteristic data representing at least one geometric characteristic of the first tooth flat;
  using the characteristic data to calculate a computer model of the patient's possible jaw motion under occlusal contact between teeth in the patient's upper and lower jaws.

The invention is advantageous in that it preferably facilitates the preparation of a dental restoration. The invention may for example allow for using one or more flats present at a patient's tooth or teeth to obtain information about the articulation of that patient. As an advantage such information about articulation may be directly calculated from geometric characteristics of the flat(s) by use of the present invention. Therefore the invention may be advantageous in that a mechanical articulator may not be required. The invention preferably also allows determining the articulation directly rather than indirectly via a mechanical and/or virtual articulator. This is because articulators typically simulate the temporomandibular joint and based on that simulation the articulation is derived, whereas the invention preferably does not require a simulation of the temporomandibular joint, but may directly calculate the articulation based on the shape of the teeth. Further the method of determining the articulation may be performed remote from of the patient and without interaction with the patient, in particular measuring of anatomic characteristics at the patient using a face bow is preferably not be required in the method of the invention. Further the invention may be advantageous in that it may help providing a relatively inexpensive dental restoration because measuring efforts, typically performed by the dentist, and manual determination of the articulated, typically performed by a dental technician, may be minimized.

The "calculation of the computer model of a possible jaw motion" for the purpose of this specification preferably relates to the use of the characteristic data in one or more computer instructions to provide data which are suitable for geometrically defining the jaw motion. Such data may for example comprise three-dimensional positions of an upper jaw relative to a corresponding lower jaw, or of an upper tooth in an upper jaw relative to a lower tooth in a corresponding lower jaw. Such data may for further comprise direction vectors for describing a displacement between an upper jaw relative to a corresponding lower jaw, or between an upper tooth in an upper jaw relative to a lower tooth in a corresponding lower jaw.

A "flat" as referred to in the present specification may be a result of abrasion of two opposing teeth on each other, for example during chewing action. It has been found that flats caused by abrasion are typically present at teeth of most patient's. Such flats typically differentiate by their curvature from the curvature of the flat surrounding tooth structure, and are even in many cases substantially planar. Also it has been found that a natural tooth typically is substantially free of natural flats such that substantially all of the present flats correspond to abrasion caused flats. It has further been found that therefore abrasion caused tooth flats may be relatively reliably identified.

A "possible jaw motion under occlusal contact between teeth in the patient's upper and lower jaws" preferably refers to a movement of a patient's jaws relative to one another that are enabled under constantly maintaining the occlusal contact. In contrast there may be a movement which is restricted under occlusal contact due to at least a tooth of each jaw engaging and blocking that movement. The possible jaw motion under occlusal contact between teeth in the patient's upper and lower jaws may also generally be referred to as "articulation".

In one embodiment the representation of the patient's first tooth is provided in a physical positive or negative model of the patient's teeth. A negative model of the patient's teeth may correspond to a dental impression taken in a patient's mouth. However the negative model may further be manufactured in a material build-up process. The build-up process may be controlled based on scan data obtained by intra-oral scanning, for example. The physical model may further be a positive plaster model which is, for example obtained from casting in the negative model. Such a positive model may also be manufactured in a material build-up process which may be controlled based on intra-oral scan data.

In another embodiment the representation of the patient's first tooth is a computer model representing (for example in the form of mathematically descriptive surface data) a surface of the patient's first tooth. Such a computer model may represent one or more further teeth, for example all teeth present in one or both jaws, and part of the gums.

In one embodiment the step of evaluating the first tooth flat comprises recognizing of a substantially planar surface area of the first tooth by a curvature of that surface area being within a predetermined range. Further in this embodiment the step of evaluating the first tooth flat may comprise recognizing a shaded surface area by its shade differentiating from an adjacent surface area.

In another embodiment the step of evaluating the first tooth flat comprises manual recognition of the first tooth flat and optically shading the first tooth flat. For example the representation of the patient's first tooth may be explored for a surface area which has a certain shading relative to other surface areas, and a surface area having such a shading may be identified as flat. The shading is preferably provided on the tooth representation, for example manually provided by a dentist or a dental technician by highlighting, for example with a color. The shading may however in an alternative method be provided on a natural tooth. The flats may thus be highlighted relative to an adjacent surface of the tooth or tooth representation. The shading may provide for maximizing the precision and or reliability of a subsequent automatic recognition of a flat. This is because the shading may provide a clear signal to an optical capturing device, like a camera for example, and thus may be recognized in detail at a minimized error level.

In a further embodiment the step of evaluating the first tooth flat comprises automatic recognition of the first tooth flat by use of a computer. For example the representation of the patient's first tooth may be explored for a surface area which has a certain curvature within a predetermined range, and a surface area having such a curvature may be identified as flat. Such exploration may be performed manually, for example at a physical model by a dental technician. Further the exploration may be performed automatically for example by a computer using a computer model obtained from previously scanning all or portions of the patient's first tooth (with the patient's first tooth for example provided in the form of a representation of the patient's tooth). However the computer may also use a computer model obtained from real-time scanning smaller portions of the patient's first tooth (with the patient's first tooth for example provided in the form of a representation of the patient's tooth).

In one embodiment the method comprises the step of determining at least one positional relationship between the upper and lower jaws in which the upper and lower jaws are under occlusal contact. The positional relationship between the upper and lower jaws may be provided manually, for example by a bite registration or by models of each the upper and lower jaw joined in a certain position. This may facilitate calculating the articulation, and thus may minimize computer processing time. The step of determining a positional relationship may further comprise detecting (for example automatically detecting) a second tooth flat at an opposite second tooth on the basis of similar characteristic data between the first and second teeth. The second tooth may be represented in a computer model. Again such a computer model may represent one or more further teeth, for example all teeth of one or both jaws, and part of the gums.

In one embodiment the characteristic data comprise at least one of:
  an inclination angle of the flat in a reference coordinate system;
  a position of the flat in the reference coordinate system;
  a curvature of the flat;
  a surface roughness of the flat;

a size of the flat;

a shape of the flat; and a normal on the flat.

The method may comprise the step of determining a motion path representing a model of a possible movement of the jaws relative to one another under occlusal contact. Thereby the motion path preferably extends along a line between a first and a different second positional relationship of the jaws. The occlusal contact may be provided between a first set of teeth in a first positional relationship, and between a different second set of teeth in a second positional relationship. The occlusal contact may for example change along the motion path from the first set of teeth to the second set of teeth, and eventually may be provided at further different sets of teeth in between. The motion path may be represented by a line or by multiple lines (for example lines which together form a polygon). A line may be defined by any suitable parameters, for example by the positions of two points on the line, or by the position of one point on the line and a slope or direction vector. Such a line may thus be a virtual line represented by parameters defining the line.

In another embodiment the method may comprise the step of determining a motion surface representing a model of a possible movement of the jaws relative to one another under occlusal contact. The motion surface may extend between at least three different positional relationships between the jaws. A surface may also be defined by any suitable parameters, for example by the positions of three points on the surface, or by the position of one point on the surface and two slopes or direction vectors. Such a surface may thus be a virtual surface represented by parameters defining the surface.

In one embodiment the motion path or motion surface is used for determining a shape of at least part of a dental restoration. For example a jaw motion may be simulated virtually and the motion of points on one or more teeth opposite the tooth to be restored may be used to define at least part of an occlusal surface of the dental restoration. For example at least a partial representation of a tooth opposite of the dental restoration may be virtually moved on the motion path or on the motion surface to virtually carve away a volume of a preliminary representation of the dental restoration.

In a further embodiment the method comprises the step of providing a representation of a preliminary representation of a dental restoration. The representation of a preliminary representation may be selected from a database holding a plurality of standard tooth shapes, for example.

In another embodiment the method comprises the steps of determining a plurality of tooth flats at a patient's teeth or representations thereof, and evaluating the plurality of tooth flats to provide characteristic data representing a multiplicity of geometric characteristics related to the individual tooth flats. Thereby the accuracy of the determination of the articulation maximized. This may further help minimizing computer processing time required for such determination. In a further aspect the invention relates to a system for preparing a dental restoration. The system comprises software adapted for performing the method of the invention. The system may further comprise at least one of a scanner, a CAD computer and a manufacturing machine for a dental restoration.

In still a further aspect the invention relates to a use of one or more tooth flats for providing a computer model of a patient's possible jaw motion under occlusal contact between teeth in the patient's upper and lower jaws. In this use a first tooth flat at a representation of the first patient's tooth is determined and evaluated to provide characteristic data representing at least one geometric characteristic of the first tooth flat, and wherein the characteristic data is used to calculate the possible jaw motion. This preferably makes the use of a mechanical or virtual articulator unnecessary.

DETAILED DESCRIPTION OF THE INVENTION

The Figures describe an exemplary workflow of the method according to the invention.

Figure 1:
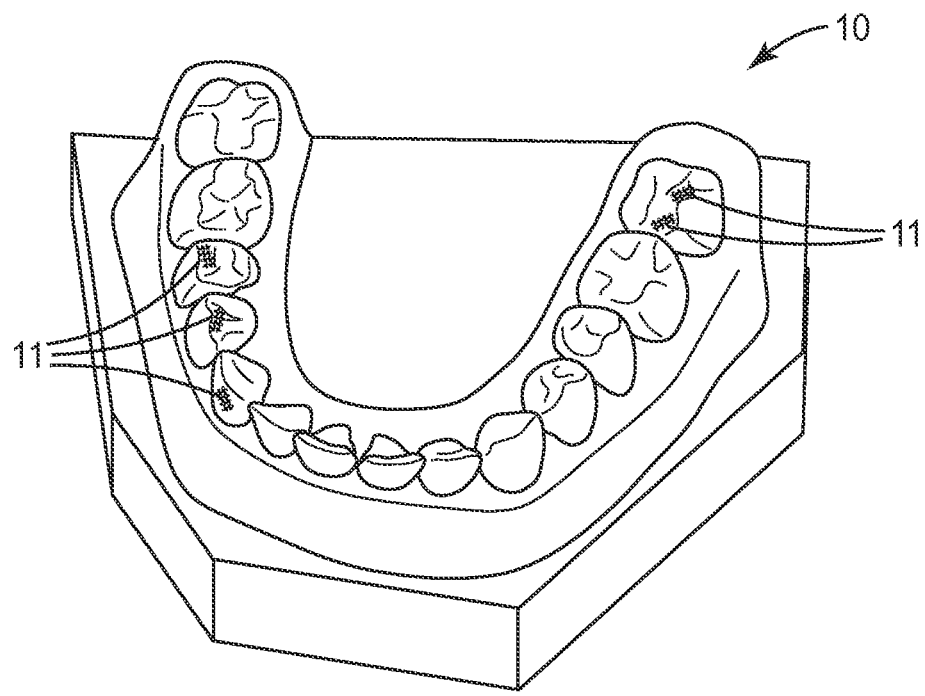
FIG. 1 is a perspective top view of a plaster model of a patient's teeth indicating tooth flats according to an embodiment of the invention.

FIG. 1 shows a plaster model 10 representing a patient's teeth. Such a plaster model can be typically obtained by taking a dental impression from the patient's teeth, and using the impression to form the plaster model. The dental impression is typically formed by placing a hardenable, initially liquid or pasty, impression material in a patient's mouth, allowing the material to harden in place, and finally removing the hardened, preferably elastic, material from the patient's mouth. Thus a negative impression of the patient's teeth may be formed that may then be used as a mold for the plaster. A plaster preparation may for example be filled in the negative impression and allowed to harden therein so that finally a plaster model may be obtained like the one shown in the Figure. The person skilled in the art will recognize that instead of or in addition to the plaster model the negative impression may be directly used in the method of the invention, although the use of a positive model may have certain advantages.

The teeth in the plaster model 10 have tooth flats 11 which in the example are indicated as patterned area. The person skilled in the art will recognize that more flats may be present at one or more of the patient's teeth, and that only some may be highlighted and illustrated in this example.

The plaster model may be placed in a scanner, for example a dental scanning device, which may capture the shape of at least a portion of the plaster model (or the negative impression). Such a scanner is for example available under the designation Lava™ Scan ST from 3M ESPE AG, Germany, or under the designation D700 from 3Shape A/S, Denmark, or under the designation 5Series from Dental Wings, Canada. Thus the scanner may indirectly capture at least a portion of the patient's teeth. The person skilled in the art will further recognize that the shape of the patient's teeth may be scanned directly in a patient's mouth, for example by use of an intra oral scanner. Such an intra-oral scanner is for example available under the designation Lava™ COS from 3M, USA, or under the designation E4D from D4D Technologies, USA, or under the designation CEREC Bluecam from Sirona Dental Systems GmbH, Germany. The scanner preferably uses the captured shape to provide scan data which represent the outer surface of at least a portion of the patient's teeth.

The scan data may be processed in a computer which is adapted to recognize the flats, for example to automatically recognize the flats. For example the software may recognize contiguous surface areas having a certain minimum size and a certain maximum curvature as flats.

Further the flats may be manually recognized and physically highlighted before scanning, for example during an inspection of the plaster model by a person. Such a highlighting may for example be made by marking with a color which differs from the color of the plaster model. The so prepared plaster model may be scanned with the scanner not only capturing the shape of the model, but further capturing the shading or color of the model surface. A direct highlighting of the natural teeth in a patient's mouth as well as the highlighting of the impression is possible. For highlighting natural teeth a substance may be used that is transparent under normal light conditions, but optically detectable under special light conditions. Such a substance may for example comprise fluorescent particles that are substantially not visible under visible light of a wavelength between 400 nm to 700 nm, but can be made visible for the scanner under light of a shorter wavelength (for example under infrared light). The substance may further be generally harmless and water soluble so that it can be rinsed away easily when desired. Such a substance may further be used for highlighting flats at the plaster model or the negative impression. Further the computer aided and manual recognition of the flats may be combined. This may help maximizing the reliability of recognizing the flats.

Figure 2:
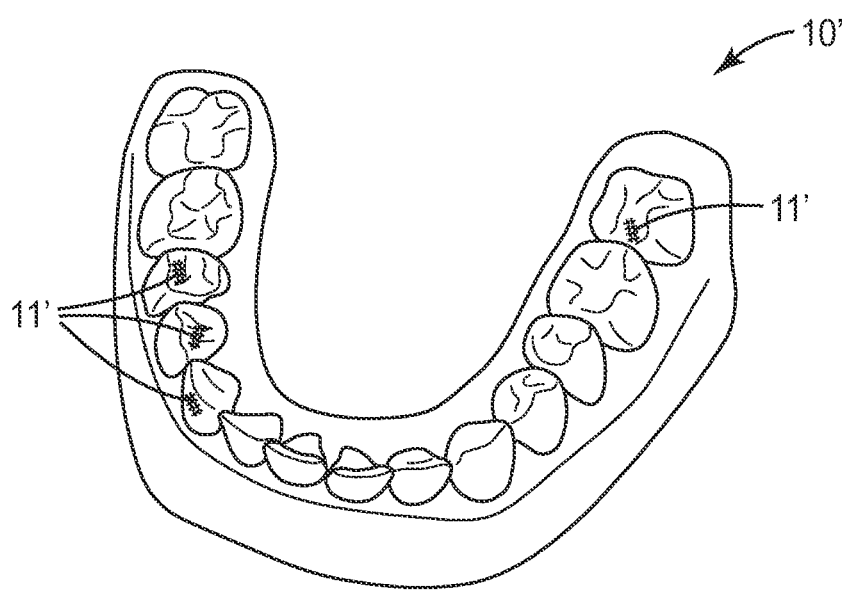
FIG. 2 is a perspective view of a computer representation of a patient's teeth indicating tooth flats according to an embodiment of the invention.

FIG. 2 shows a surface representation 10' of the patient's teeth as it may be generated by the computer based on the scan data. The surface representation 10' comprises flats 11' recognized by the computer which in the Figure are highlighted for better illustration. The computer may be adapted to display the surface representation 10' on a computer screen, and further to display the flats as highlighted areas to make the flats clearly visible to a user. However the flats may be also be recognized within the computer without visualizing them. The computer may further allow a user to select or deselect individual flats from the flats displayed. For example the computer may allow the user to select a flat or multiple flats that should be used in a subsequent step of the method of the invention, or to deselect a flat for excluding it from use in a subsequent method step. A certain flat may for example further be deselected if it was erroneously recognized as a flat. Such a function may for example be implemented such that a user can position a mouse cursor on the flat and clicking it for selection or deselection. Selected and deselected flats may be indicated to the user by different colors and/or patterns, for example.

A recognized or selected flat may further be evaluated to provide corresponding characteristic data about the flat. Such characteristic data may for example comprise at least one of the following data:
  shape of the flat;
  size (for example area) of the flat;
  position of the flat relative to a reference coordinate system;
  an inclination angle of the flat in one or more dimensions of a reference coordinate system; and
  a normal on the flat.

The characteristic data may be used to determine one or more constraints in a possible movement of a patient's upper and lower jaw relative to each other. Further the characteristic data may be used to define one or more positional relationships between the upper and lower jaw, for example a position in which the jaws may be in occlusal contact, meaning a position in which at least one tooth of the upper jaw and at least one tooth of the lower jaw can be in contact in the patient's mouth.

Figure 3:
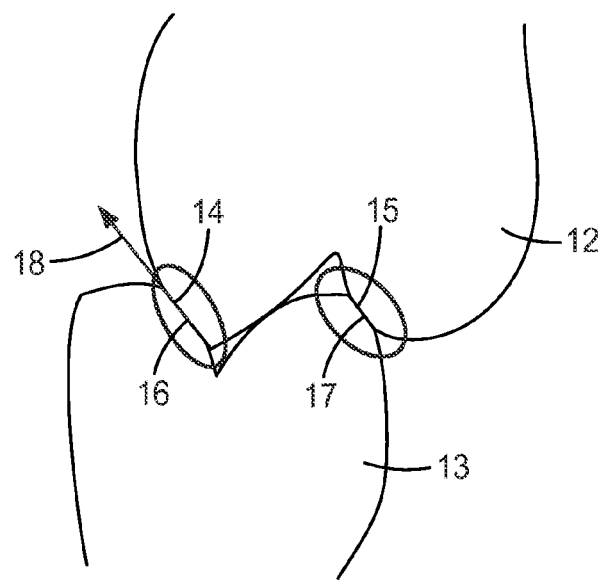
FIG. 3 is a schematic view illustrating two teeth in occlusal contact at tooth flats.

FIG. 3 shows an upper tooth 12 of an upper jaw and a lower tooth 13 of a lower jaw. The upper tooth 12 has a first flat 14 and a second flat 15. The positions of the first and second flats 14, 15 also define positions in which the upper and lower jaws can be in occlusal contact (as illustrated) because the flats 14, 15 may result from abrasion between teeth of the upper and lower jaw which requires such contact.

Further the shape and size of a flat may be used to detect a flat of a similar shape and size at an opposite tooth which may provide a positional relationship between the upper and lower jaws. In the example the lower tooth 13 has first and second flats 16, 17 which approximately correspond in size and shape to the first and second flats 14, 15 of the upper tooth 12. Thus the first and second flats 14, 15 and the flats 16, 17 may be assigned or matched to one another. Such an assignment or matching may be performed virtually, for example by computer processing. In this way one possible positional relationship between the upper and lower jaws may be determined.

In another example an occlusal position may be provided by a bite registration. Typically a bite registration comprises at least a partial impression of the patient's teeth in at least one occlusal position. Such a bite registration may be provided by a dentist, for example. The bite registration may be scanned directly, or indirectly from a plaster model molded by use of the bite registration. A surface representation of the bite registration may be electronically matched with surface representations of teeth of the upper and lower jaw. Thus the positional relationship between the upper and lower jaw in at least one occlusal position may be determined.

The inclination angle of a flat may define a direction in which the upper and lower jaws are movable relative to one another when the jaws are in a certain positional relationship. This is indicated by the arrow 18 in the Figure. The flats 14, 15, 16, 17 are all inclined at a similar angle from which a certain direction of movement between the jaws under occlusal contact may be assumed.

The computer may perform an iterative process in which possible positional relationships and possible movements of the upper and lower jaw relative to each other are determined by use of the characteristic data. Preferably a plurality of flats may be used to determine a multiplicity of characteristic data. Thus a multiplicity of occlusal positions and directions of movement may be obtained to form articulation data.

Such articulation data may be used to create an articulation profile defining a motion path on which the jaws may move, while in occlusal contact, relative to one another. For defining the motion path at least two occlusal positions may be used with the motion path being defined by a straight line between the positions. Further such motion path may correspond to a spline defined by several positions in which the upper and lower jaws may be in occlusal contact. The occlusal positions used to define the articulation profile may be determined by help of the directions of movement, for example by detecting a second occlusal position in the proximity of a certain direction of a first occlusal position. A plurality of articulation profiles may be used to provide an articulation surface. The articulation surface may be defined by a surface between at least two articulation profiles. Such a surface may be approximated by a set of straight lines (or curved lines, for example obtained from a spline) extending between the profiles. Thus the articulation surface may be approximated by a set of lines forming a virtual three-dimensional wireframe. In this way an approximate representation of the articulation of a patient's jaws may be determined in at least a certain range without the use of an articulator.

Further a generic model of a temporomandibular joint may be defined by use of the articulation data. For example from the shape of one or more articulation profiles or the articulation surface approximate joint positions of the temporal bone and the mandible of the upper and lower jaws respectively may be determined.

In a further example plaster models of upper and lower jaws of a patient may be brought in occlusal contact with one another. An occlusal contact as it can occur in a patient's mouth may be determined by positioning the models such that a flat of one tooth contacts an opposing tooth or a corresponding flat of that opposing tooth. This may for example be done manually by an operator. The plaster models of the patient's jaw may further be brought in occlusal contact with one another in a plurality of different positional relationships of the models relative to one another. Each positional relationship of the plaster models may be captured, for example by scanning the plaster models while in occlusal contact. Thus a plurality of positional relationships of the jaws relative to one another may be determined and used to calculate a possible jaw motion or articulation.

Figure 4:
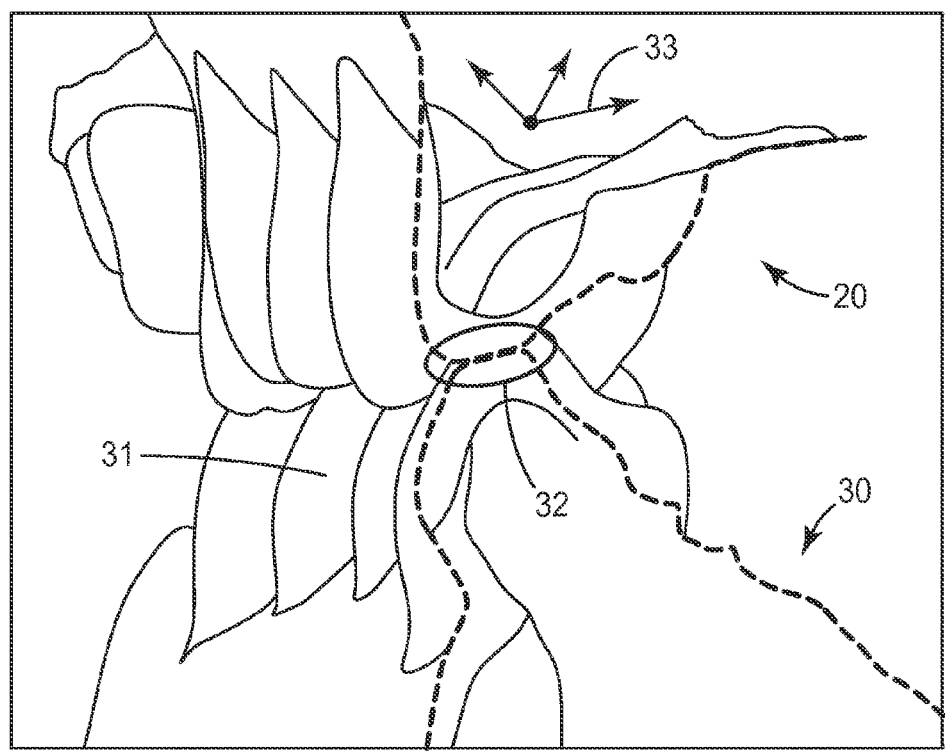
FIG. 4 is a perspective view of a computer representation of a portion of the upper and lower jaws of a patient used for preparation a dental restoration according to an embodiment of the invention.

FIG. 4 illustrates a computer representation of an upper jaw 20 and a lower jaw 30. The lower jaw 30 comprises a computer representation of a dental restoration 31. A preliminary representation of the dental restoration may be obtained from a database holding a plurality different standardized tooth shapes. The preliminary representation of the dental restoration may for example be selected from the database on the basis of the location of the tooth to be restored, for example dependent on whether the tooth is located in the upper or lower jaw and dependent on the position (front, left or right side) in the jaw. The preliminary representation of the dental restoration may be changed at the lateral sides by computer aid, for example by use of a dental CAD system, so that it pleasantly fits inline with adjacent teeth. The occlusal side of the preliminary representation of the dental restoration may be initially oversized such that it overlaps with one or more opposing teeth in at least one positional relationship of the jaws under virtual occlusal contact (indicated by numeral 32). The overlap may be automatically removed by computer aid such that the preliminary representation of the dental restoration is trimmed. Thereby the preliminary representation may obtain the negative shape of the opposing tooth or teeth or a proximate of it. The removal of overlap may be repeated at different positional relationships of the upper and lower jaws relative to one another. For example the different positional relationships of the jaws may be selected according to one or more motion paths and/or to one or more motion surfaces (as indicated by the array of arrows 33). Thus the preliminary representation of the dental restoration may be virtually cut due to a relative movement between the preliminary representation and the opposing teeth. Therefore the trimmed preliminary representation may not collide with opposing teeth in a variety of positional relationships of the jaw. The skilled person will recognize that the removal of the overlap may comprise providing a small space between the trimmed dental restoration representation and the opposing tooth or teeth. This may avoid for interferences between the final dental restoration and opposing teeth, for example which may arise due to tolerances during manufacturing of the dental restoration or during placement of the dental restoration in a patent's mouth.

The skilled person will be able to provide further methods of shaping a representation of a dental restoration. For example the preliminary representation of the dental restoration may be obtained by automatic or manual design, by scanning at least a portion of the tooth to be restored, or a combination thereof. Further instead of trimming an oversized representation an undersized preliminary representation may be virtually grown until it virtually abuts the surface of one or more of the opposing teeth. It may also be possible to provide a final representation of a dental restoration without starting at a preliminary representation. For example the constraints provided by the teeth opposing the tooth to be restored may be used to automatically create a representation of the occlusal face of the dental restoration. This representation of the occlusal face may then be automatically completed by lateral faces, for example shaped according to constraints provided by a tooth or teeth adjacent the tooth to be restored.

The trimmed, grown, automatically created, or preliminary representation of the dental restoration may further be provided with fissure structures, for example manually by using a CAD System, to make the final dental restoration resemble a natural tooth.

After shaping the representation of the dental restoration a final representation of the dental restoration may be obtained in the form of computer data. Such computer data may be used to provide machine instructions for controlling a machine, for example a milling, grinding or rapid prototyping machine, to manufacture a physical dental restoration.

The physical dental restoration may be a precursor of a pre-sintered ceramic material which may be sintered and optionally veneered or provided with a glaze to obtain the final dental restoration, for example. However the physical dental restoration may already correspond to the final dental restoration for example milled or ground from a finally sintered ceramic block.

The invention claimed is:

1. A computer implemented method comprising the steps of:
   determining a first tooth flat at a representation of a first patient's tooth;
   evaluating, using a computer processor, the first tooth flat to provide characteristic data representing at least one geometric characteristic of the first tooth flat;
   using the characteristic data, stored in a non-transitory computer readable storage medium operably coupled to a computer processor, to calculate a computer model of the patient's possible jaw motion under occlusal contact between teeth in the patient's upper and lower jaws;
   determining a motion path representing a model of a possible movement of the jaws relative to one another under the occlusal contact, wherein the motion path extends along a line between a first and a different second positional relationship of the jaws;
   obtaining a preliminary representation of a dental restoration, wherein the preliminary representation is initially oversized such that the preliminary representation overlaps with one or more opposing teeth under the occlusal contact along the motion path; and
   using the motion path for determining a shape of at least part of the dental restoration by virtually moving at least a partial representation of a tooth opposite of the dental restoration on the motion path to virtually trim the preliminary representation in order to remove the overlap.

2. The method of claim 1, wherein the step of evaluating the first tooth flat comprises recognizing of a planar surface area of the first tooth by a curvature of that surface area being within a predetermined range and/or recognizing of a shaded surface area by its shade differentiating from an adjacent surface area.

3. The method of claim 1, wherein the step of evaluating the first tooth flat comprises manual recognition of the first tooth flat and optically shading the first tooth flat.

4. The method of claim 1, wherein the step of evaluating the first tooth flat comprises automatic recognition of the first tooth flat by use of a computer.

5. The method of claim 1, further comprising the step of determining at least one positional relationship between the upper and lower jaws in which the upper and lower jaws are under occlusal contact.

6. The method of claim 5, wherein the step of determining a positional relationship comprises detecting a second tooth flat at an opposite second tooth on the basis of similar characteristic data between the first and second teeth.

7. The method of claim 1, wherein the characteristic data comprises at least one of
- an inclination angle of the flat in a reference coordinate system;
- a position of the flat in the reference coordinate system;
- a curvature of the flat;
- a surface roughness of the flat;
- a size of the flat; and
- a shape of the flat.

8. The method of claim 7, further comprising the step of determining a motion surface representing a model of a possible movement of the jaws relative to one another under occlusal contact, wherein the motion surface extends between at least three different positional relationships between the jaws.

9. The method of claim 1, comprising the steps of determining a plurality of tooth flats at representations of a patient's teeth, and evaluating the plurality of tooth flats to provide characteristic data representing a multiplicity of geometric characteristics related to the individual tooth flats.

10. A non-transitory computer readable storage medium, comprising computer executable instructions, that when executed by a processor perform the method as set forth in claim 1.

11. The method of claim 1, wherein the obtaining step includes obtaining the preliminary representation from a database of standardized tooth shapes.

12. The method of claim 1, wherein the obtaining step includes obtaining the preliminary representation by scanning at least a portion of a tooth to be restored.

13. The method of claim 1, wherein the using the motion path step includes virtually trimming the preliminary representation such that the trimmed preliminary representation does not collide with opposing teeth in a variety of positional relationships of the jaw.

* * * * *